US00PP29697P2

(12) United States Plant Patent
Eggleton

(10) Patent No.: US PP29,697 P2
(45) Date of Patent: Sep. 18, 2018

(54) ***LAVANDULA* 'GHOSTLY PRINCESS'**

(50) Latin Name: *Lavandula hybrida*
Varietal Denomination: GHOSTLY PRINCESS

(71) Applicant: Steven Eggleton, Wonga Park (AU)

(72) Inventor: Steven Eggleton, Wonga Park (AU)

( * ) Notice: Subject to any disclaimer, the term of this patent is extended or adjusted under 35 U.S.C. 154(b) by 0 days.

(21) Appl. No.: 15/732,044

(22) Filed: Sep. 8, 2017

(30) Foreign Application Priority Data

Jul. 12, 2017 (AU) ..... PBR 2017/202

(51) Int. Cl.
*A01H 5/02* (2018.01)

(52) U.S. Cl.
USPC ..... Plt./445

(58) Field of Classification Search
USPC ..... Plt./445
See application file for complete search history.

*Primary Examiner* — Annette H Para
(74) *Attorney, Agent, or Firm* — Cassandra Bright

(57) ABSTRACT

A new and distinct *Lavandula* cultivar named 'GHOSTLY PRINCESS' is disclosed, characterized by distinctively grey-green foliage and a moderately dense plant habit. The new variety produces light pink terminal bracts. The new variety is a *Lavandula*, normally produced as an outdoor garden or container plant.

2 Drawing Sheets

Figure 1:
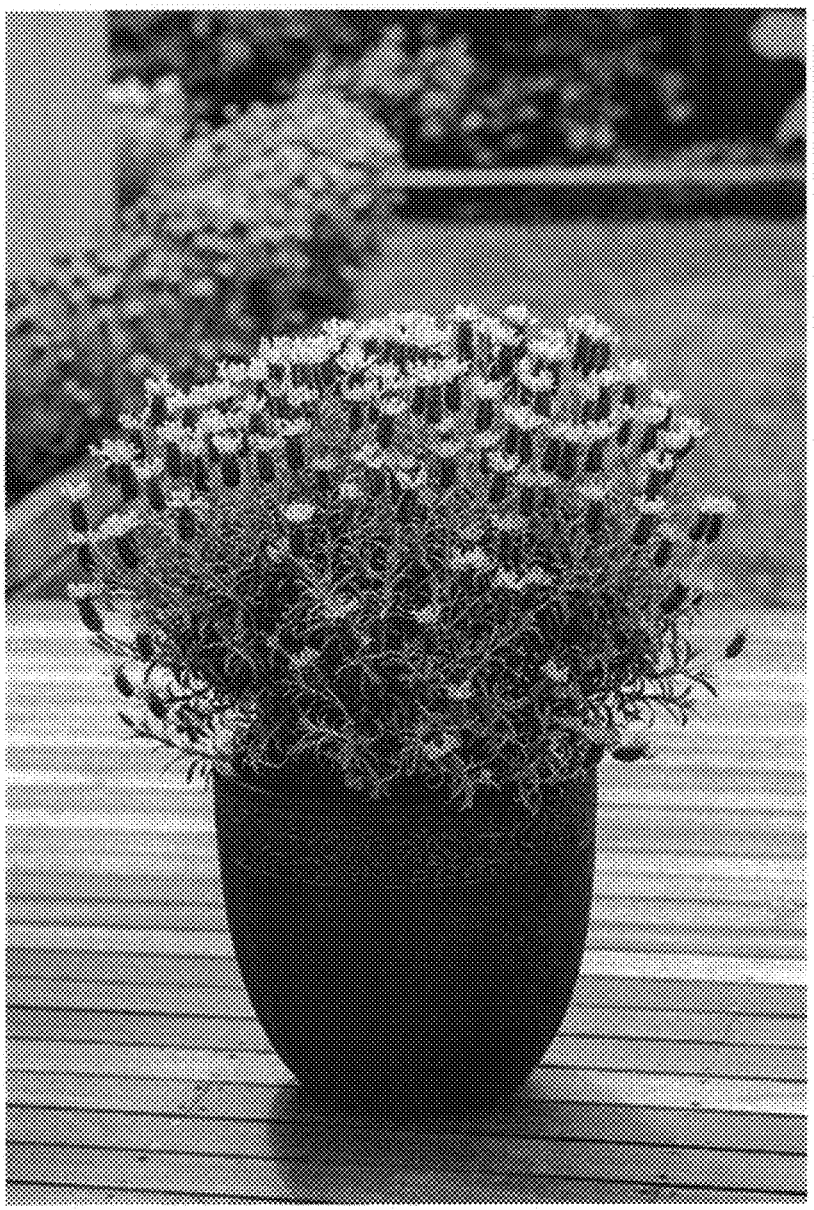

Latin name of the genus and species: *Lavandula hybrida.*
Variety denomination: 'GHOSTLY PRINCESS'.

BACKGROUND OF THE INVENTION

The new *Lavandula* cultivar is a product of a planned breeding program conducted by the inventor, Steven Eggleton, in Wonga Park, Australia. The objective of the breeding program was to produce new *Lavandula* varieties for ornamental commercial applications. The cross resulting in this new variety was made during November of 2012.

The parent varieties are both proprietary, undistributed seedlings from the inventor's own breeding program. The new variety was first selected in September of 2013 by the inventor in a group of seedlings resulting from the 2012 crossing, in a research greenhouse in Wonga Park, Australia. The inventor made further observations of the new variety, making a final selection in October of 2014.

Asexual reproduction of the new cultivar was performed by vegetative cuttings. This was performed at a research greenhouse in Wonga Park, Australia in October of 2014 and has shown that the unique features of this cultivar are stable and reproduced true to type through at least 5 successive generations.

SUMMARY OF THE INVENTION

The cultivar 'GHOSTLY PRINCESS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GHOSTLY PRINCESS' These characteristics in combination distinguish 'GHOSTLY PRINCESS' as a new and distinct *Lavandula* cultivar:

1. Silver foliage.
Strong iridescent pink infertile bract coloration.

2. Light pink infertile bracts.
3. Medium dense plant habit.

Plants of the new cultivar 'GHOSTLY PRINCESS' are similar to plants of the seed parent in most horticultural characteristics, however, plants of the new cultivar 'GHOSTLY PRINCESS' differ in the following:

1. Foliage of the new variety is significantly more silver-grey in color.
2. Infertile bracts of the new variety are shorter than those of the seed parent.
3. Infertile bract color of the new variety is lighter pink than the seed parent.

Plants of the new cultivar 'GHOSTLY PRINCESS' are similar to plants of the pollen parent in most horticultural characteristics, however, plants of the new cultivar 'GHOSTLY PRINCESS' differ in the following:

1. Infertile bract color of the new variety is light pink, infertile bract color of the pollen parent is purple.
2. Plant density of the new variety is medium, plant density of the pollen parent is weak.

COMMERCIAL COMPARISON

Plants of the new cultivar 'GHOSTLY PRINCESS' are comparable to the variety *Lavandula* 'Sweetberry Ruffle' U.S. Plant Pat. No. 22,447. The two *Lavandula* varieties are similar in most horticultural characteristics; however, the new variety 'GHOSTLY PRINCESS' differs in the following:

1. Foliage of the new variety is significantly more silver-grey in coloration.
2. Infertile bract color of the new variety is darker pink with more lavender tones than the comparator.

Plants of the new cultivar 'GHOSTLY PRINCESS' can also be compared to the commercial variety *Lavandula* 'Strawberry Ruffles' U.S. Plant Pat. No. 22,490. These varieties are similar in most horticultural characteristics; however 'GHOSTLY PRINCESS' differs in the following;

1. Foliage of the new variety is significantly more silver-grey in coloration.
2. Infertile bract color of the new variety is much lighter pink with more lavender tones than the comparator.

BRIEF DESCRIPTION OF THE PHOTOGRAPHS

The accompanying photograph in FIG. 1 illustrates in full color a typical plant of 'GHOSTLY PRINCESS' grown outdoors in Australia.

Figure 2:
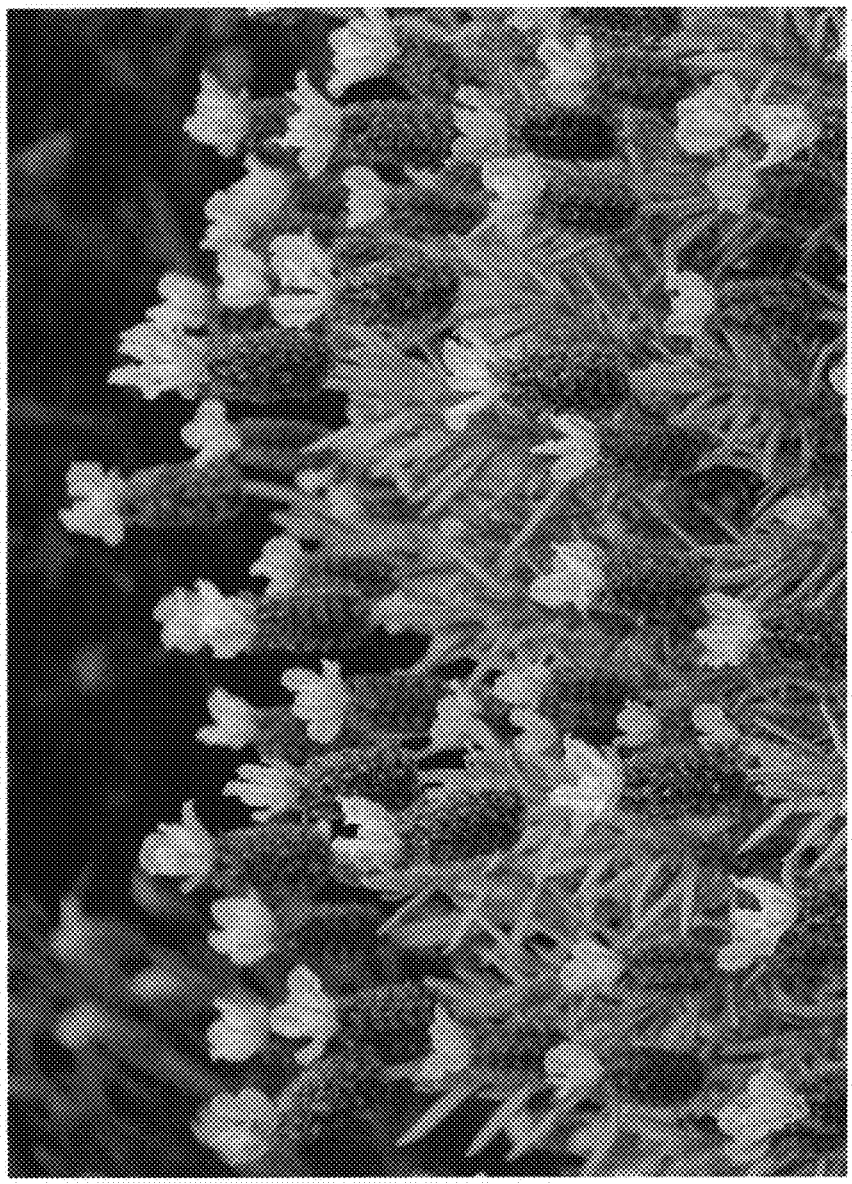

FIG. 2 is a close up view of the inflorescence. Age of the plant photographed is approximately 40 weeks from a rooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'GHOSTLY PRINCESS' plants grown outdoors during, Spring, and Summer in Watsonville, Calif. The growing temperature ranged from approximately 10° C. to 33° C. during the day and from about 5° C. to 18° C. during the night. General light conditions are bright, normal sunlight. Measurements and numerical values represent averages of typical plant types.

Botanical classification: *Lavandula hybrida* 'GHOSTLY PRINCESS'.

PROPAGATION

Time to initiate roots: About 10-14 days at approximately 21° C.

Time to produce a rooted cutting: About 25-35 days at 21° C.

PLANT

Age of plant described: Approximately 40 weeks from rooted cutting.

Plant spread: Approximately 29 cm.

Plant height: Approximately 34 cm, to top of flowering plane. Approximately 25 cm to top of foliar plane.

Growth rate: Moderate.

Length of primary lateral branches: Approximately 15 to 20 cm.

Diameter of lateral branches: Approximately 3 mm.

Quantity of lateral branches: About 20 to 30.

Plant habit: Moderately dense upright plant.

Branches/stems:

*Juvenile color*.—Near Greyed-Green 193C.

*Semi-ripe color*.—Near Greyed-Purple N187D.

*Mature color*.—Near Greyed-Green 197A covered in glaucous layered colored 192D.

*Texture/pubescence*.—Soft and very short pubescence on youngest stems, mature stem canescent, oldest stem canescent, not woody or rough.

Internode length: Approximate 1.0 to 1.5 cm. (mature lateral stem).

FOLIAGE

Leaf:

*Arrangement*.—Opposite.

*Leaf type*.—Simple.

*Quantity*.—Approximately 8 to 14 per linear cm.

*Average length*.—Approximately 3.0 cm. (range 1.5 cm to 4.0 cm).

*Average width*.—Average 3 mm.

*Shape of blade*.—Linear.

*Apex*.—Acute.

*Base*.—Truncate.

*Attachment*.—Sessile.

*Margin*.—Entire.

*Texture of surfaces*.—Softly pubescent all surfaces, short pubescence.

*Leaf fragrance*.—Moderate resinous scent.

*Color*.—Young foliage upper side: Near Greyed-Green 194A, tinged 188D. Young foliage under side: Near Greyed-Green 194A, tinged 188D. Mature foliage upper side: Near Greyed-Green 191B, tinged 188D. Mature foliage under side: Near Greyed-Green 191C, tinged 188D.

*Venation*.—Type: Pinnate reticulate. Venation color upper side: Indistinguishable from leaf blade. Venation color under side: Near Greyed-Green 194C.

*Petiole*.—Absent.

FLOWER

Bloom period: Main Flush late winter to late spring. Spot flowering occurs throughout Summer and Fall.

Inflorescence:

*Form*.—Small single flower in verticillasters arranged in spikes. 6 to 10 rows of flowers. Flowers have small bracts, and large showy terminal bracts. Number of individual flowers per spike: Approximately 40 to 100. Corolla shape: Salverform. Petal Number: 5. Petals Fused or Unfused: Fused at base. Petal Shape: Top 2 lobes obovate, lower 3 lobes ovate. Petal Margin: Entire. Petal Surfaces: Glabrous. Length: Approximately 6 mm (corolla tube). Diameter: Approximately 4 mm.

*Inflorescence size, excluding terminal bracts*.—Length: Approximately 3 to 4 cm. Width: Approximately 2 cm. Shape: Cylindrical. Coloration of individual flowers and entire spikes, excluding terminal bracts: Immature: Near Purple N81B. Mature: Near Purple-Violet N80B. Fading: Near Purple-Violet N81C. Calyx Width: 2 mm. Calyx Length 7 mm. Calyx Shape: Tubular. Calyx color: RHS Greyed-Green 190A. Bract shape: Orbicular. Bract apex: Cuspidate. Bract Color: Greyed-Green 190A.

Terminal bracts (sterile):

*Quantity*.—Usually 4 per inflorescence.

*Length*.—Approximately 2.5 cm.

*Width*.—Approximately 1.3 cm.

*Form and shape*.—Petaloid, irregular oblong.

*Margin*.—Entire and undulating.

*Surface*.—Smooth.

*Appearance*.—Matte.

*Apex*.—Broadly Acute.

*Base*.—Obtuse.

*Vein pattern*.—Reticulate.

*Duration on plant*.—Approximately 12 weeks, with good color. Persistent.

Fragrance: Moderate resinous scent.

REPRODUCTIVE ORGANS

Androecium:

*Stamens*.—4.

*Anther shape*.—Linear.

*Anther length*.—Approximately 0.5 mm.

*Anther width*.—About 0.2 mm.

*Anther color*.—Near RHS Greyed-Purple N187D.

*Pollen quantity*.—Pollen production not observed.

Pistil:

*Number*.—1.

*Length*.—Approximately 3 mm.

*Style*.—Length: Approximately 2 mm. Color: Near RHS White N155A.

*Stigma*.—Length: Approximately 0.3 mm. Shape: Linear. Color: Near RHS Greyed-Purple N187A. Ovary: Minute and immeasurable.

OTHER CHARACTERISTICS

Disease/pest resistance: Neither resistance nor susceptibility to the normal diseases and pests of *Lavandula* has been observed.

Drought tolerance and cold tolerance: Hardy perennial. Tolerates high temperature to at least 32° C. Tolerates low temperatures to −12° C. While specific drought tolerance has not been observed, once plants are established very little water is necessary to maintain plants.

Fruit/seed production: Fruit and seed production not observed.

What is claimed is:

1. A new and distinct cultivar of *Lavandula* plant named 'GHOSTLY PRINCESS' as herein illustrated and described.

* * * * *